(12) United States Patent
Barber et al.

(10) Patent No.: US 11,820,799 B2
(45) Date of Patent: Nov. 21, 2023

(54) *MALASSEZIA* FACTOR WITH ANTIBIOTIC ACTIVITY

(71) Applicant: University of Oregon, Eugene, OR (US)

(72) Inventors: Matthew Barber, Eugene, OR (US); Caitlin Kowalski, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 17/827,244

(22) Filed: May 27, 2022

(65) Prior Publication Data

US 2022/0380416 A1    Dec. 1, 2022

Related U.S. Application Data

(60) Provisional application No. 63/194,785, filed on May 28, 2021.

(51) Int. Cl.
| | | |
|---|---|---|
| *C07K 14/00* | (2006.01) | |
| *C07K 14/37* | (2006.01) | |
| *A61P 31/04* | (2006.01) | |
| *A61K 38/00* | (2006.01) | |

(52) U.S. Cl.
CPC .............. *C07K 14/37* (2013.01); *A61P 31/04* (2018.01); *A61K 38/00* (2013.01)

(58) Field of Classification Search
CPC .......... C07K 14/37; A61P 31/04; A61K 38/00
See application file for complete search history.

(56) References Cited

PUBLICATIONS

Li et al., "Skin Commensal *Malassezia globosa* Secreted Protease Attenuates *Staphylococcus aureus* Biofilm Formation," *Journal of Investigative Dermatology*, vol. 138, pp. 1137-1145, 2018.
Saunders et al., "*Malassezia* Fungi Are Specialized to Live on Skin and Associated with Dandruff, Eczema, and Other Skin Diseases," *PLoS Pathogens*, vol. 8, No. 6, Article e1002701, 2012 (4 pages).
Wu et al., "Genus-Wide Comparative Genomics of *Malassezia* Delineates Its Phylogeny, Physiology, and Niche Adaptation on Human Skin," *PLoS Genetics*, vol. 11, No. 11, Article e1005614, 2015 (26 pages).

*Primary Examiner* — Jeanette M Lieb
(74) *Attorney, Agent, or Firm* — Klarquist Sparkman, LLP

(57) ABSTRACT

Compositions including an antibiotic factor from *Malassezia* are provided. In some examples, the compositions include a *Malassezia* exoproduct, a *Malassezia* cell-free supernatant, or a *Malassezia* cell and a pharmaceutically acceptable carrier. Methods of treating an infection in a subject, such as a *Staphylococcus* infection are also provided.

15 Claims, 11 Drawing Sheets

Ancestral (White, W)   Evolved (Yellow, Y)

MALASSEZIA FACTOR WITH ANTIBIOTIC ACTIVITY

CROSS REFERENCE TO RELATED APPLICATION

This claims the benefit of U.S. Provisional Application No. 63/194,785, filed May 28, 2022, which is incorporated herein by reference in its entirety.

ACKNOWLEDGMENT OF GOVERNMENT SUPPORT

This invention was made with government support under Grant No. R35 GM133652 awarded by the National Institutes of Health. The government has certain rights in the invention.

FIELD

This disclosure relates to compositions with antibiotic activity and methods of their use, particularly for inhibiting *Staphylococcus aureus*.

BACKGROUND

As pathogens encounter new host environments, abiotic factors such as temperature, pH, and nutrient supply influence pathogen survival and disease outcomes. Equally important are the biotic factors encountered by invading pathogens including host cellular and humoral defenses as well as host-associated microbes. As a result, these resident microbes exert strong selective pressures driving pathogen evolution. Currently, examples of these influential microbial interactions are largely limited to those between bacteria, and it remains unclear how interactions with resident fungi influence pathogen evolution and disease outcomes Recent studies have illustrated that fungi are able to modulate bacterial growth, virulence, and antibiotic sensitivity. The human skin is a major barrier to infection and is colonized by an estimated $10^6$ to $10^9$ microorganisms per $cm^2$, of which the relative abundance of fungi is estimated to be 10 times greater in some regions than observed within the gut microbiome. The gram positive bacterial pathogen *Staphylococcus aureus* is a chronic asymptomatic colonizer of the nose in humans, but only transiently colonizes the skin. *S. aureus* skin colonization is a major risk factor for skin and soft tissue infections that amount to approximately a half of a million annual hospitalization in the United States. Additionally, *S. aureus* skin colonization and toxin production have been associated with multiple cancers. Thus, understanding obstacles to *S. aureus* skin colonization is a point of great interest in promoting human health.

SUMMARY

Disclosed herein are antimicrobial (e.g., antibiotic) compositions derived from the fungus *Malassezia*. Such compositions are useful for treating or inhibiting bacterial growth or infection, particularly growth of, or infection with *Staphylococcus aureus*. In embodiments, the disclosed compositions include a *Malassezia* exoproduct, a *Malassezia* cell free supernatant (CFS), or a *Malassezia* cell; and a pharmaceutically acceptable carrier. In particular examples, the *Malassezia* is *Malassezia sympodialis*, *Malassezia restricta*, or *Malassezia globosa*. In some examples, the *Malassezia* exoproduct has one or more characteristics of heat resistance, binding to non-polar molecules, and pH sensitivity (for example, antimicrobial activity at pH of about 6 or less).

In embodiments, the composition inhibits growth and/or infection with a *Staphylococcus* species, for example, *S. aureus*, methicillin-resistant *S. aureus*, vancomycin-resistant *S. aureus*, *S. caprae*, *S. epidermidis*, *S. haemolyticus*, or *S. warneri*. In some examples, the composition inhibits growth of a *Staphylococcus* species by at least 10-fold compared to a control.

In some embodiments, the composition includes about 0.01%-10% w/w, 0.01-10% v/v, or 0.01-10% w/v of the *Malassezia* exoproduct, cell free supernatant, or cells. In additional embodiments, the composition further includes one or more additional antibiotic compounds. In some embodiments, the composition is formulated for topical administration, such as a solution, gel, ointment, cream, or suspension. In some examples, the pharmaceutically acceptable carrier is a base including a plurality of inactive ingredients.

Also provided herein are methods of treating or inhibiting bacterial growth, infection, and/or skin colonization in a subject. The methods include administering a disclosed composition to the subject. In some embodiments, the bacteria is a *Staphylococcus* species (for example, *S. aureus*, methicillin-resistant *S. aureus*, vancomycin-resistant *S. aureus*, *S. caprae*, *S. epidermidis*, *S. haemolyticus*, or *S. warneri*). In some examples, the subject has a bacterial skin infection, such as a skin infection with *S. aureus*, methicillin-resistant *S. aureus*, or vancomycin-resistant *S. aureus*.

In some embodiments, the composition is administered orally or intravenously. In other embodiments, the composition is administered topically, for example to the skin, such as at the site of a skin infection. In some examples, the methods include administering an additional antibiotic therapy to the subject, for example, prior to, concurrently with, or following treatment with the composition.

The foregoing and other features of the disclosure will become more apparent from the following detailed description, which proceeds with reference to the accompanying figures.

BRIEF DESCRIPTION OF THE DRAWINGS

FIG. 1A is an image showing *S. aureus* spotted on agar plates adjacent to 72 hour *Malassezia* colonies and grown for 24 hours. *S. aureus* cannot grow up to the colony. FIG. 1B is a graph showing that *S. aureus* colony forming units (CFUs) per mL were not significantly reduced after 2 hour treatment with cell-free supernatant (CFS) collected from *M. furfur* and mixed 1:1 with fresh media (50% CFS). CFS from *M. pachydermatis* resulted in a small but significant reduction in *S. aureus* CFUs/mL and CFS from *M. sympodialis* resulted in a significant, large (>100-fold) reduction in *S. aureus* CFUs/mL. FIG. 1C is a graph showing that *S. aureus* colony forming units (CFUs) per mL were reduced after 2 hour treatment with cell-free supernatant (CFS) collected from *M. sympodialis* (Ms), *M. restricta* (Mr), or *M. globosa* (Mg).

FIG. 2A is a heat-map showing forming units enumerated to calculate the proportion of bacteria surviving the indicated CFS treatment relative to the media control. Se: *S. epidermidis*; Sc: *S. caprae*; Sho: *S. hominis*; Sl: *S. lugdunensis*; Sw: *S. warneri*; Sca: *S. capitis*; Sa: *S. aureus*; Sha: *S. haemolyticus*. FIG. 2B is a graph showing CFU/ml of *S. aureus* (strain HFH) and six *S. epidermidis* strains treated with 50% CFS from *M. sympodialis* (strain KS269) or pH-matched media control (mDixon) for 6 hours.

FIG. 3A is a graph showing that toxicity of CFS collected from *M. sympodialis* KS269 was not abolished after boiling (30 min., 98° C.). Adjustment of the CFS pH from pH 5.4-5.6 to pH 6 with NaOH reduced CFS toxicity to *S. aureus*. The toxic effector was removed from the CFS following exposure to a non-polar resin. FIG. 3B is a graph showing treatment of *S. aureus* with CFS was bactericidal after 3 hours, resulting in >10,000-fold reduction in *S. aureus* CFUs. In contrast to wild-type (WT) *S. aureus*, a clean deletion mutant lacking fatty acid kinase (ΔfakA) was only slightly sensitive to treatment with *M. sympodialis* CFS.

FIG. 4A is a schematic diagram of protocol for experimental evolution of *S. aureus* exposed to 50% CFS from *M. sympodialis*. FIG. 4B is a graph of recovered CFUs from *S. aureus* strain C199 exposed to a control pH matched media condition (n=1) or 50% CFS (n=3) for 12 passages. The grey box indicates the difference between the recovered ancestor CFUs from control (top) and +50% CFS (bottom) conditions at each day. FIG. 4C is an image of Ancestral, WT-like white isolates (left) and the evolved, CFS-resistant hyperpigmented yellow isolates (right). FIG. 4D is a graph of recovered CFU/mL of pH-matched media treated (mDixon) or +50% CFS treated white and yellow colonies from EVOL-P1 replicate from passage 12. FIG. 4E is a schematic diagram of Sa-Rel protein with mutations identified in the C199 strain from the experimental evolution (EVOL-P1, -P2, P3) and the mixed-biofilm experiment (IsoA) and from the additional HFH strain used in experimental evolution (HFH EVOL-P3). HD: hydrolase domain, SYNTH: synthetase domain, TGS: ThrRS, GTPase, and SpoT domain, ACT/RRM: Aspartokinase, Chorismate mutase and TyrA/RNA Recognition Motif domain.

FIG. 6A is an image of an 11 mm NativeSkin® explant biopsy. FIG. 6B shows detection of red fluorescent protein (RFP)-expressing *S. aureus* after 24 hours on human skin biopsy at 24 hours. FIG. 6C is a graph showing *S. aureus* recoverable CFU on skin explants after 24 hours of *S. aureus* colonization followed by treatment with pH control or CFS mixed 1:1 with PBS across three independent donors.

DETAILED DESCRIPTION

I. Terms

Figure 1A:
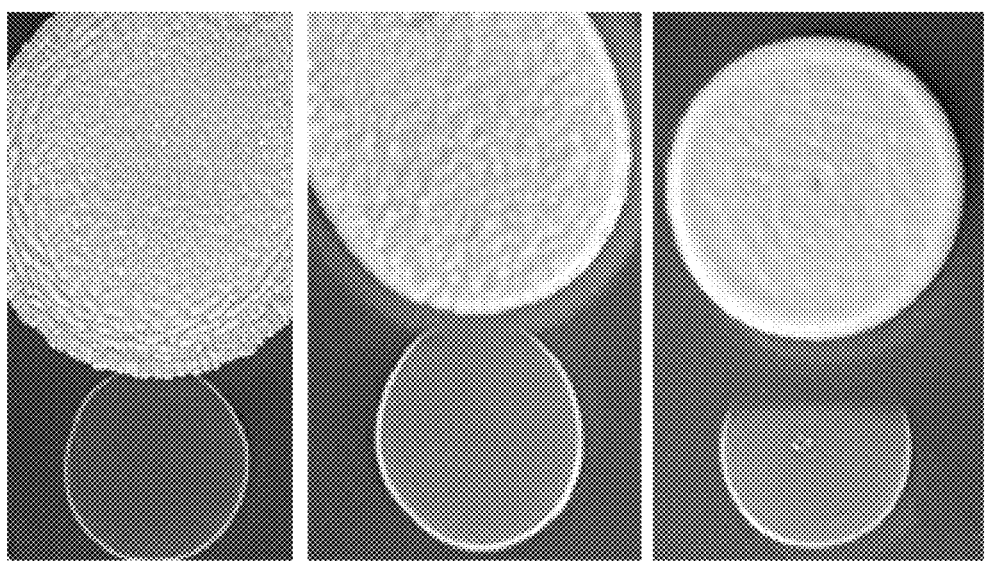
FIGS. 1A-1C show that *Malassezia* exoproducts inhibit *S. aureus*.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B.

Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

Administer: As used herein, administering a composition (e.g. an antibiotic or antimicrobial composition) to a subject means to give, apply or bring the composition into contact with the subject. Administration can be accomplished by any of a number of routes, such as, for example, topical, oral, subcutaneous, intramuscular, intraperitoneal, intravenous, intrathecal or intramuscular.

Antibiotic: A substance often produced by or derived from certain fungi, bacteria, and other organisms, that can kill or inhibit the growth of other microorganisms. Antibiotics can also be synthetically produced.

Base: As used herein, the term "base" refers to non-active or inactive ingredients included in a composition, such as non-active ingredients suitable for preparing a cream, ointment, or gel.

Cell free supernatant (CFS): A liquid preparation from a cell culture (such as a culture of *Malassezia* cells) that is substantially free of intact cells and/or cellular debris (e.g., less than about 2% or less than about 1% of the total preparation is cells and/or debris). CFS typically is prepared by centrifuging and/or filtering a cell culture to pellet cells and cellular debris and collecting the supernatant.

Effective amount: An amount of an agent or composition that alone, or together with a pharmaceutically acceptable carrier and/or one or more additional agents, induces the desired response. Effective amounts of an agent can be determined infection, and/or skin colonization. Effective amounts also can be determined through various in vitro, in vivo, or in situ assays, including, but not limited to those described herein.

Exoproduct: An extracellular product produced by a cell, such as a *Malassezia* cell. In some examples, an exoproduct is a protein, lipid, nucleic acid, exosome, small molecule or other biological product that is secreted or released by a cell, such as a *Malassezia* cell.

Inactive or non-active ingredient: As used herein, the term "inactive ingredient" or "non-active ingredient" refers to components that are not required to be disclosed by the U.S. Food and Drug Administration as being added to provide a pharmaceutical effect. Inactive or non-active ingredients are added for other purposes, such as thickening, gelling, preserving, colorizing, odorizing, deodorizing, moisture retaining, drying, solubilizing, and the like. The inactive ingredients, however, may nonetheless provide a health benefit.

Inhibiting bacterial growth: Reducing or eliminating bacterial replication and/or spread, in vitro or in vivo. Inhibition need not be complete inhibition. In some embodiments, inhibition of bacterial growth is inhibition of at least 10%, at least 20%, at least 30%, at least 40%, at least 50%, at least 60%, at least 70% or at least 80%.

Isolated: An "isolated" or "purified" biological component (such as a nucleic acid, peptide, protein, or other component) has been substantially separated, produced apart from, or purified away from other biological components for example, other chromosomal and extrachromosomal DNA and RNA, proteins, and/or cells. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins.

The term "isolated" or "purified" does not require absolute purity; rather, it is intended as a relative term. Thus, for example, an isolated biological component is one in which the biological component is more enriched than the biological component is in its standard environment or a production vessel. Preferably, a preparation is purified such that the biological component represents at least 50%, such as at least 70%, at least 90%, at least 95%, or greater, of the total biological component content of the preparation.

*Malassezia*: A genus of fungi found on the skin of humans and other animals. It is typically commensal, but can cause opportunistic infections, such as seborrheic dermatitis or atopic dermatitis. Exemplary *Malassezia* species include *M. dermatis, M. furfur, M. globosa, M. pachydermatis, M. restricta*, and *M. sympodialis*. In particular examples, the *Malassezia* species is *Malassezia sympodialis*. *M. sympodialis* is a common commensal of normal human skin microbiota; however, it can cause skin disorders such as *pityriasis versicolor*, seborrheic dermatitis, and atopic dermatitis in some situations.

Exemplary reference *Malassezia* genomes and strains are known and are publicly available. Exemplary strains include *M. sympodialis* KS269, *M. sympodialis* ATCC 96803, *M. sympodialis* ATCC 42132, *M. globosa* ATCC MYA-4612D-5, *M. globosa* ATCC MYA-4612, and *M. restricta* ATCC MYA-4611.

Pharmaceutically acceptable carrier: In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. *Remington: The Science and Practice of Pharmacy*, 22$^{nd}$ ed., London, UK: Pharmaceutical Press (2013), describes compositions and formulations suitable for pharmaceutical delivery of one or more therapeutic compositions, such as one or more antibiotic compounds.

*Staphylococcus*: A genus of gram-positive spherical bacteria that occur in microscopic clusters and produce exotoxins. In 1884, Rosenbach described two pigmented colony types of staphylococci and proposed the appropriate nomenclature: *Staphylococcus aureus* (yellow) and *Staphylococcus albus* (white). The latter species is now named *Staphylococcus epidermidis*. More than 20 species of *Staphylococcus* exist, including *S. aureus, S. auricularis, S. borealis, S. capitis, S. caprae, S. epidermidis, S. hominis, S. haemolyticus, S. lugodunensis*, and *S. warneri*.

*S. aureus* forms a fairly large yellow colony on rich medium. By comparison, *S. epidermidis* forms a relatively small white colony. *S. aureus* is often hemolytic on blood agar while *S. epidermidis* is non-hemolytic. Staphylococci are facultative anaerobes that grow by aerobic respiration or by fermentation that yields principally lactic acid. The bacteria are catalase-positive and oxidase-negative. *S. aureus* can grow at a temperature range of 15° C. to 45° C. and at NaCl concentrations as high as 15 percent. Nearly all strains of *S. aureus* produce the enzyme coagulase. In contrast, nearly all strains of *S. epidermidis* lack this enzyme. Thus, strains of *S. epidermidis* are often referred to as coagulase-negative staphylococci.

In some examples *Staphylococcus* is *S. aureus*, which is usually a commensal of the human microbiota, but is also an opportunistic pathogen that can cause skin infections (including abscesses), respiratory infections, meningitis, toxic shock syndrome, and sepsis. *S. aureus* has become resistant to many antibiotics. Thus, in some examples, *S. aureus* also includes antibiotic-resistant *S. aureus*, such as methicillin-resistant *S. aureus* (MRSA) and/or vancomycin-resistant *S. aureus* (VRSA).

Subject: Living multi-cellular vertebrate organism, a category that includes vertebrates, including human and non-human mammals.

II. Antibiotic Compositions

*Malassezia* is the dominant fungal genus on human skin. Interactions between *Malassezia* and bacteria are described herein, including identification of one or more compounds secreted by *Malassezia* that exhibit antibiotic effects. In particular examples, the one or more compounds inhibit growth of *S. aureus* (including MRSA), *S. caprae, S. epidermidis, S. haemolyticus*, and/or *S. warneri*. In other examples, the one or more compounds exhibit a bactericidal activity.

Provided herein are exoproducts produced by *Malassezia* species (such as *M. sympodialis, M. restricta*, or *M. globosa*) capable of inhibiting growth of *Staphylococcus* (including *S. aureus*), e.g., exhibiting antimicrobial activity. In some examples, the antimicrobial factor is a compound produced by and/or secreted by *Malassezia*. In some examples, the *Malassezia* is *M. sympodialis, M. restricta*, or *M. globosa*. In some embodiments, the antimicrobial factor exhibits one or more properties including heat resistance (for example, retention of antimicrobial 98° C. or higher), binding to non-polar molecules (such as a non-polar resin), and pH sensitivity (e.g., active only at pH of about 6 or less). In some embodiments, the antimicrobial factor has a molecular weight of about 2000 Da or less (e.g., based on binding to non-polar resin as described in Example 3). In other examples, the antimicrobial factor may form aggregates of about 30 kDa or more (e.g., as described in Example 3). In some embodiments, the antimicrobial factor (such as the *Malassezia* exoproduct) may be a lipid or other non-polar molecule. In other embodiments, the antimicrobial factor (such as the *Malassezia* exoproduct) is not a protein. In additional embodiments, a fatty acid kinase (fakA) mutant of *S. aureus* is resistant to the antimicrobial factor.

In some embodiments, the antimicrobial factor inhibits growth of one or more *Staphylococcus* species, such as inhibits growth of one or more of *S. aureus, S. caprae, S. epidermidis, S. haemolyticus*, and *S. warneri* compared to a control. In some examples, a disclosed antimicrobial factor inhibits growth of one or more of *S. aureus, S. caprae, S. epidermidis, S. haemolyticus*, and *S. warneri* by at least about 10-fold (such as at least about 10-fold, at least about 50-fold, at least about 100-fold, at least about 500-fold, at least about 1000-fold, at least about 5000-fold, at least about 10,000-fold, or more) compared to a control, such as untreated *S. aureus, S. caprae, S. epidermidis, S. haemolyticus*, or *S. warneri*. In other examples, a disclosed antimicrobial factor specifically inhibits growth of one or more of

*S. aureus, S. caprae, S. epidermidis, S. haemolyticus*, and *S. warneri*, for example, inhibits growth of one or more of *S. aureus, S. caprae, S. epidermidis, S. haemolyticus*, and *S. warneri* by at least about 10-fold (such as at least about 10-fold, at least about 50-fold, at least about 100-fold, at least about 500-fold, at least about 1000-fold, at least about 5000-fold, at least about 10,000-fold, or more), but inhibits growth of other *Staphylococcus* species by less than about 10-fold (such as less than about 5-fold, less than about 2-fold, or less than 50%) compared to a control (such as the untreated *Staphylococcus* species).

In some embodiments, provided herein are compositions including a *Malassezia* exoproduct (such as a *M. sympodialis* exoproduct, a *M. restricta* exoproduct, or a *M. globosa* exoproduct) capable of inhibiting growth of *Staphylococcus* (for example, one or more of *S. aureus*, MRSA, VRSA, *S. caprae, S. epidermidis, S. haemolyticus*, and *S. warneri*) and a pharmaceutically acceptable carrier. In other embodiments, provided herein are compositions including a cell-free supernatant from a *Malassezia* species (such as *M. sympodialis, M. restricta*, or *M. globosa*) and a pharmaceutically acceptable carrier. In still further embodiments, provided herein a compositions including *Malassezia* (such as *M. sympodialis*) cells and a pharmaceutically acceptable carrier. In some examples, the composition includes live *Malassezia* cells (such as active or dormant *M. sympodialis, M. restricta*, or *M. globosa* cells).

The pharmaceutical compositions comprising the antimicrobial (e.g., antibiotic) compounds disclosed herein may be formulated in a variety of ways depending, for example, on the mode of administration and/or on the location and type of infection to be treated. For example, such pharmaceutical compositions may be formulated as pharmaceutically acceptable salts. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

Certain embodiments of the pharmaceutical compositions comprising antibiotic compounds as described herein may be formulated in unit dosage form suitable for individual administration of precise dosages. The amount and route of administration of a therapeutic compound administered will depend on the subject being treated, the type and severity of the infection, and the manner of administration, and is known to those skilled in the art. Within these bounds, the formulation to be administered will contain a quantity of the antibiotic compounds disclosed herein in an amount effective to achieve the desired effect in the subject being treated (e.g., reducing or eliminating *Staphylococcus* pathogens).

In some embodiments, the composition includes about 0.01-10% (w/v or v/v) of the active composition (exoproduct, cell-free supernatant, or cells), for example, about 0.01-0.1%, about 0.05%-0.5%, about 0.25%-1%, about 0.75%-1.5%, about 1-2.5%, about 2-5%, about 3-6%, about 4-8%, about 5-7.5%, or about 6-10%. In other embodiments, the composition includes about $10^2$-$10^9$ *Malassezia* cells (such as *M. sympodialis, M. restricta*, or *M. globosa* cells), for example, about $10^2$-$10^4$ cells, about $10^3$-$10^5$ cells, about $10^4$-$10^6$ cells, about $10^5$-$10^7$ cells, about $10^6$-$10^8$ cells, or about $10^7$-$10^9$ cells.

In some embodiments, the composition includes one or more additional antibiotic compounds, for example, one or more of clindamycin, erythromycin, tetracycline, minocycline, doxycycline, penicillin, ampicillin, carbenicillin, methicillin, cephalosporins, vancomycin, bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, and inezolid.

For topical compositions (e.g., liquids, lotions, creams, ointments, pastes, and the like), the disclosed compositions may include carriers such as solid carriers (e.g., finely divided solids such as talc, clay, microcrystalline cellulose, silica, alumina, and the like), liquid carriers (e.g., water, dimethyl sulfoxide (DMSO), alcohols, glycols, or water-alcohol/glycol blends, optionally with the aid of non-toxic surfactants), and/or thickeners (e.g., synthetic polymers, fatty acids, fatty acid salts and esters, fatty alcohols, modified celluloses, or modified mineral materials).

For topical administration, the disclosed compositions (e.g., *Malassezia* exoproduct(s), CFS, or cells) may be formulated as solutions, gels, ointments, creams, suspensions, etc. Particular embodiments of formulations for use in the methods described herein include a therapeutically effective amount of the compound, a topical base, an antioxidant, an emollient, and an emulsifier. A person of skill in the art will appreciate that a therapeutically effective amount of the compound may vary, but typically the therapeutically effective amount is from 0.01% to 10% (w/w).

Embodiments of a topical compositions include a base including a plurality of inactive ingredients. In some embodiments, the base is a topical cream or topical gel base. The inactive ingredients may include, but are not limited to, acrylates/C10-30 alkyl acrylate crosslinked polymer (e.g., Carbopol® Ultrez 21 polymer, Lubrizol Advanced Materials, Cleveland, Ohio), colloidal silver (e.g., Bio-Active Silver Hydrosol™, Natural Immunogenics, Inc., Pompano Beach, Fla.), fulvic liquid minerals, potassium sorbate, vegetable glycerin (USP grade), citric acid, water, sodium hydroxide, crosslinked poly(acrylic acid) (e.g., Carbopol® Ultrez 30 polymer), caprylyl glycol, ethylhexylglycerin, or any combination thereof. In some embodiments, sodium hydroxide functions as an emulsifier and buffer, and may thicken a polymer gel base. Colloidal silver may be utilized as an antimicrobial agent. In some embodiments, the water is purified water or positively charged acidic water. The fulvic minerals may be any of various compositions extracted from fulvic mineral bases. The topical base may include polyethylene glycol having a selected molecular weight. Particular embodiments comprise a polyethylene glycol having a molecular weight of from 3000 to 8000 daltons as a topical base. In certain embodiments, the formulation is an ointment, and may further include a water-miscible solvent, such as a polyalkylene glycol having an average molecular weight of from 200 daltons to 600 daltons. In certain embodiments the water-miscible solvent comprises PEG-400, and even more particularly PEG-400 substantially free of impurities.

The base may include one, all, or any of the above-listed inactive ingredients, or other inactive ingredients, in any desired ratio to produce a desired viscosity, a desired dry time on the skin, a desired scent, a desired shelf life, a desired biological activity, or any other desired characteristic of property of a topical gel or cream composition. In some embodiments, the base may further comprise 0.1-5 wt % ethanol to facilitate drying of the gel of cream on a subject's skin and/or to achieve a desired viscosity. The disclosed topical compositions may be packaged in any suitable manner. For example, the topical composition may be packaged into a pump bottle (e.g., an airless pump bottle), a squeeze bottle, a plastic tube, a metallic tube, an automatic dispensing tube, an ampoule, a jar, a tin, or any other packaging material capable of containing and, optionally, preserving potency and/or efficacy of the active agents of the topical composition.

Topical formulations for use as described herein also can include a penetration enhancer, such as dimethyl isosorbide, propylene glycol, or combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, a tocopherol, and combinations thereof, with particular embodiments comprising butylated hydroxytoluene as an antioxidant; and an optional colorant.

In one embodiment, the formulation is a solution. In another embodiment, the formulation is a gel. In another embodiment, the formulation is a suspension. In yet another embodiment, the formulation is a cream or ointment. One embodiment is any of the aforementioned formulations in a kit for topical or local administration. In one embodiment, the formulation is a liquid, for example a homogeneous liquid or a suspension, sold in a bottle which dispenses the formulation as drops or a liquid film (for example from an applicator tip that contacts a target area of the skin to dispense the liquid substantially only on a target area of the skin to be treated). In one embodiment, the formulation is a cream or ointment, sold in a tube which dispenses the formulation to a target area of the skin. In another embodiment, the compound is provided in a viscous liquid (such as carboxylmethylcellulose, hydroxypropylmethycellulose, polyethylene glycol, glycerin, polyvinyl alcohol, or oil containing drops) for rubbing into the skin. The formulations may have preservatives or be preservative-free (for example in a single-use container).

Systemic formulations include those designed for administration by injection, for example, subcutaneous, intravenous, intramuscular, intrathecal or intraperitoneal injection, as well as those designed for transdermal, oral, or pulmonary administration. Useful injectable preparations include sterile suspensions, solutions or emulsions of the active compound(s) in aqueous or oily vehicles. The compositions may also contain formulating agents, such as suspending, stabilizing and/or dispersing agent or activating agents for activating the prodrug. The formulations for injection may be presented in unit dosage form, for example, in ampules or in multidose containers, and may contain added preservatives. They may also be provided in syringes, for example syringes with needles from injection of the drug into the skin, for example at the site of a bacterial infection (such as a S. aureus infection).

Alternatively, the injectable formulation may be provided in powder form for reconstitution with a suitable vehicle, including but not limited to sterile pyrogen free water, buffer, dextrose solution, etc., before use. The powder can include an activating agent for a prodrug, which activates the prodrug when the powder is solubilized in a vehicle. To this end, the active compound(s) may be dried by any art-known technique, such as lyophilization, and reconstituted prior to use.

The topical formulation may be prepared in a variety of forms. Solids are generally firm and non-pourable and commonly are formulated as a bar or stick, or in particulate form; solids may be opaque or transparent, and optionally may contain solvents (including water and alcohol), emulsifiers, moisturizers, emollients, fragrances, dyes/colorants, preservatives and active ingredients. Creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Lotions and creams also may optionally contain moisturizers and emollients (especially in the case of skin care products), as well as fragrances, dyes/colorants, preservatives and active ingredients. Gels/serums may be prepared with a range of viscosities, from thick (high viscosity) to thin (low viscosity) and differ principally from lotions and creams in that gels/serums are usually clear rather than opaque. Like lotions and creams, gels/serums often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Suitable emulsifiers for use in the formulations include, but are not limited to, Incroquat Behenyl TMS (behentrimonium methosulfate, cetearyl alcohol), non-ionic emulsifiers like polyoxyethylene oleyl ether, PEG-40 stearate, ceteareth-12 (e.g., Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations or mixtures thereof.

Other suitable additional and adjunct ingredients which may be included in the formulations include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

III. Methods of Use

Also provided are methods of inhibiting bacterial growth, infection, and/or skin colonization, comprising administering a disclosed antimicrobial factor(s) to a subject. In some examples, the bacteria is a *Staphylococcus* species, such as *S. aureus* or methicillin-resistant *Staphylococcus aureus* (MRSA).

The composition including the antimicrobial factor can be administered to a subject in need of treatment using any suitable means known in the art. Methods of administration include, but are not limited to, topical, intradermal, intramuscular, intraperitoneal, parenteral, subcutaneous, rectal, intranasal, inhalation, or oral administration. In particular examples, the composition is administered topically. In other examples, the composition is administered orally or intravenously. In some embodiments, the composition is administered orally, intravenously, or topically.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

In some embodiments the disclosed topical compositions are suitable for topical application to the skin of a subject, wherein the subject is a human or non-human animal. In some embodiments, the topical composition is suitable for use by an adult or child, such as a child two years of age or older. The topical composition may be used to treat or inhibit bacterial skin infection, such as infection with *S. aureus*. To use, the subject may apply an amount (typically a thin layer) of the topical composition sufficient to cover a portion of or an entire affected area, wherein the affected area is an area with bacterial infection (such as an area with dermatitis, cellulitis, or an abscess). The infection may be intradermal or subcutaneous. In some embodiments, the topical composition is rubbed or massaged into the affected skin or is applied to a wound.

In some embodiments, the composition is administered at least once per day, for example, 1-6 times daily (such as 1, 2, 3, 4, 5, or 6 times per day). In other embodiments, the composition is administered less frequently, such as every other day, every three days, once per week, or less. The administration may be for a sufficient period of time to treat or inhibit a bacterial infection (such as a *S. aureus* infection), for example for 2 or more days (such as 2, 3, 4, 5, 6, 7, 8, 9, 10, 11, 12, 13, 14 days or more). In one embodiment, the composition is provided in a sustained release format, such as an adhesive patch which is applied to the skin (such as an affected area). Such adhesive patches generally have an adhesive layer, which is applied to a person's skin, a depot or reservoir for holding the active agent(s), and an exterior surface that prevents leakage of the active agent from the depot. The exterior surface of a patch is typically non-adhesive.

In particular examples, prior to, during, or following administration of a disclosed composition, the subject can receive one or more additional antibiotic therapies. Examples of such antibiotic therapies include, but are not limited to clindamycin, erythromycin, tetracycline, minocycline, doxycycline, penicillin, ampicillin, carbenicillin, methicillin, cephalosporins, vancomycin, and bacitracin, streptomycin, gentamycin, chloramphenicol, fusidic acid, ciprofloxin and other quinolones, sulfonamides, trimethoprim, dapsone, isoniazid, teicoplanin, avoparcin, synercid, virginiamycin, cefotaxime, ceftriaxone, piperacillin, ticarcillin, cefepime, cefpirome, rifampicin, pyrazinamide, ciprofloxacin, levofloxacin, enrofloxacin, amikacin, netilmycin, imipenem, meropenem, inezolid, pharmaceutically acceptable salts thereof, and prodrugs thereof. Combinations of these therapies can also be administered to a subject. Generally, the additional antibiotics of use in the methods disclosed herein are formulated for topical administration; however, other routes of administration can also be utilized.

In some examples, the subject has an infection with *S. aureus* (such as skin infection or a systemic infection with *S. aureus*). In some examples, the subject has an infection with an antibiotic-resistant *S. aureus* (such as MRSA or VRSA). Treatment with a disclosed *Malassezia* antimicrobial factor can in some examples result in the antibiotic-resistant *S. aureus* becoming antibiotic-sensitive again, for example, sensitive to a β-lactam antibiotic, such as methicillin or vancomycin. Thus, in some examples, the methods include treating a subject with a MRSA or VRSA infection with a disclosed composition including one or more *Malassezia* antimicrobial factors, followed by treatment with a β-lactam antibiotic. In some examples, treatment with the β-lactam antibiotic is at least about 4 hours after treatment with a disclosed composition (for example, at least about 8 hours, at least about 12 hours, at least about 24 hours, at least about 2 day, at least about 4 days, or more, after treatment with a disclosed composition).

EXAMPLES

The following examples are provided to illustrate certain particular features and/or embodiments. These examples should not be construed to limit the disclosure to the particular features or embodiments described.

Example 1

Materials and Methods

Strains and growth conditions: *Malassezia* species were maintained on/in mDixon media (1 liter: 36 g Malt Extract, 20 g Ox-bile, 10 mL Tween 40, 6 g Peptone, 2 mL Glycerol, 2 mL Oleic Acid, and 15 g Agar) at 30° C. *S. aureus* strains were maintained on/in Tryptic Soy Broth (TSB) or Agar (TSA) at 37° C. unless otherwise stated. Other staphylococci were maintained in the same manner as *S. aureus*.

Yeast-bacteria in vitro antagonism assays: For adjacent growth assays, the yeast strains were grown in 12.5 mL mDixon in shaking flasks for 96 h at 30° C., 180 rpm. Yeast were collected through centrifugation at 5,000×g for 2 min and resuspended in fresh mDixon media to an OD600 of 1. 10 μL of yeast suspension was plated on mDixon agar for 72 h at 30° C. *S. aureus* 5 mL overnight cultures inoculated with a single colony were centrifuged at 5,000×g for 1 min to collect bacterial cells and resuspend in mDixon to an OD600 of 0.1. Adjacent to the mature yeast colony, 15 μL of the bacterial cell suspension was plated. Spots were dried at room temperature and then incubated for 24-48-h at 30° C.

To generate cell-free supernatant (CFS), yeast strains were grown in 12.5 mL mDixon in shaking flasks for 96-h at 30° C., 180 rpm. Supernatant was collected through centrifugation at 5,000×g for 2 min and yeast cells discarded. The pH of the supernatant was measured and an mDixon pH-match was generated by addition of HCl. Both the pH-matched mDixon and supernatant were filter-sterilized using a 10 mL syringe fitted to a 0.22 μm syringe driven filter. Both the CFS and pH-matched mDixon were stored at 4° C. for a maximum of 2 weeks and warmed before use at 37° C. for 15 min.

For CFS treatment assays, *S. aureus* was grown overnight in 5 mL TSB at 37° C., 200 rpm. After ~16 hours, 1:10 dilution was from the overnight culture was made in fresh TSB and incubated for 1 h at 37° C., 200 rpm so that *S. aureus* was in late exponential phase (OD600 of ~1). *S. aureus* cells were collected through centrifugation at 5,000×g for 1 min and resuspended in mDixon. Control conditions were prepared by mixing fresh mDixon 1:1 with pH-matched and treatment conditions were prepared by mixing fresh mDixon 1:1 with CFS. *S. aureus* was inoculated into these conditions to a final OD600 of 0.02 and incubated at 37° C. for 0-6 h at 200 rpm. After incubation, the control or treatment conditions were serially diluted in sterile water and dilutions plated on TSA and incubated overnight at 37° C. to enumerate CFUs. The assay was performed similarly with different *Malassezia* species and staphylococcal species. Treatment of *Malassezia* cell-free supernatant: For boiling treatment, CFS prepared from *M. sympodialis* cultures as described above or pH-matched mDixon control was incubated in a dry heat block at 98° C. for 30 min. For pH treatment, the CFS and pH-matched control were adjusted to pH 6 through the addition of NaOH and then filter-sterilized with a 0.22 μm syringe-driven filter. For resin treatment, 1.25 mL of CFS or 1.25 mL pH-matched mDixon control were incubated at room temperature on a platform shaker at 80 rpm with 0.25 g of Bio-Rad Bio-Beads SM-2 Resin for 3 hours. After 3 hours, resin was removed and the pH was adjusted back to original pH with HCl. The resin treatment increased the pH from approximately pH 5.5 to pH 5.9. Following the treatments, *S. aureus* was exposed to untreated CFS or pH control, or the treatment groups and CFUs were enumerated as described above.

Experimental evolution of *S. aureus* with CFS: The experimental evolution was performed with *S. aureus* strain C199 (USA400) and also with *S. aureus* strain HFH (USA300). Four populations were maintained throughout the serial passaging: one control population with pH-matched mDixon and three treatment populations with *M. sympodialis* CFS mixed 1:1 with fresh mDixon media. The initial set up for the experimental evolution was similar to all other CFS treatment assays. After a 1-h subculture in TSB, *S. aureus* was collected and resuspended in mDixon. The four populations, at a volume of 0.5 mL, were inoculated to an OD600 of 0.02 and incubated at 37° C., 200 rpm for 8 hours. After 8 h, 50 μL was taken for serial dilution and CFU enumeration on TSB. The remaining 0.45 mL was inoculated into 5 mL of TSB and incubated for 15 h at 37° C., 200 rpm. *S. aureus* does not grow robustly in mDixon during the 8-h exposure, so this incubation in TSB allowed for expansion of the surviving population. After 15 h, the 1:10 subculture was performed in TSB, and the second passage was set up the same as the first. This was carried out for 12 passages. As a control during each passage, the ancestral C199 strain was also exposed to the pH control and CFS. After the passaging, aliquots from each population were inoculated onto TSA+5% sheep's blood and TSA to assess changed in colony morphology. Phenotypically diverse colonies were selected and patched on to TSA plates and subsequently tested in isolated for sensitivity to *M. sympodialis* CFS as described above.

Genome sequencing and variant calling: Colonies of interest isolated from the CFS-resistant evolved populations were selected for genome sequencing. Genome DNA was extracted with the Qiagen DNeasy® Blood & Tissue Kit following the protocol for preparation from gram positive bacteria. Specifically, lysostaphin (20 mg/mL) was included in the initial lysis steps. DNA was quantified with Qubit™ dsDNA BR Assay kit. Genome sequencing was performed through the Microbial Genome Sequencing Center (Pittsburgh, Pa.). Illumina sequencing was performed on a NextSeq 2000 platform. Variant calling was performed using breseq. *S. aureus* MW2 was the selected reference genome for *S. aureus* C199.

*S. aureus* growth curves: *S. aureus* growth curves were performed on a BioTek Synergy™ H1 monochromator-based multi-mode microplate reader in non-treated flat bottom 96-well plates. *S. aureus* grown overnight in 5 mL of TSB was subcultured 1:10 in fresh TSB for 1 h. Cells were collected through centrifugation at 5,000×g for 1 min and resuspended in fresh TSB. For 0 μg/mL oxacillin, 4 μg/mL oxacillin, and 16 μg/mL oxacillin TSB was utilized with a starting OD600 of 0.02.

*S. aureus* colonization of NativeSkin® human skin biopsy: NativeSkin® biopsies of 11 mm diameter were purchased from Genoskin Inc from three separate female donors. Each biopsy was from a healthy donor and from the abdominal region. *S. aureus* RN4220 expressing red fluorescent protein (RFP) from the plasmid pSRFPS1 was utilized for colonization. Media without antibiotic or antifungals was used for culturing the NativeSkin® biopsies, and media was changed every 24 h. *S. aureus* was inoculated in 12 μL of PBS with 10 μg/mL trimethoprim for plasmid maintenance at a cell density of ~2.5×10$^7$ cells per 12 μL. Prior to inoculated *S. aureus* was grown in TSB and washed twice with PBS. Blank biopsies inoculated with PBS were also included. Biopsies were incubated at 37° C., 5% $CO_2$ for 24 h. To confirm *S. aureus* colonization of the biopsies, biopsies were inverted in 35 mm MatTek imaging dishes with 10 mm glass diameter and imaged with a Nikon CSU-W1 SoRA Spinning Disk microscope. Biopsies were homogenized with collagenase at 37° C. followed by mechanical disruption. Serial dilutions of the homogenate were plated on TSB.

Example 2

Skin-Resident Yeast *Malassezia* Produces Exoproducts Toxic to *Staphylococcus aureus*

Figure 1B:
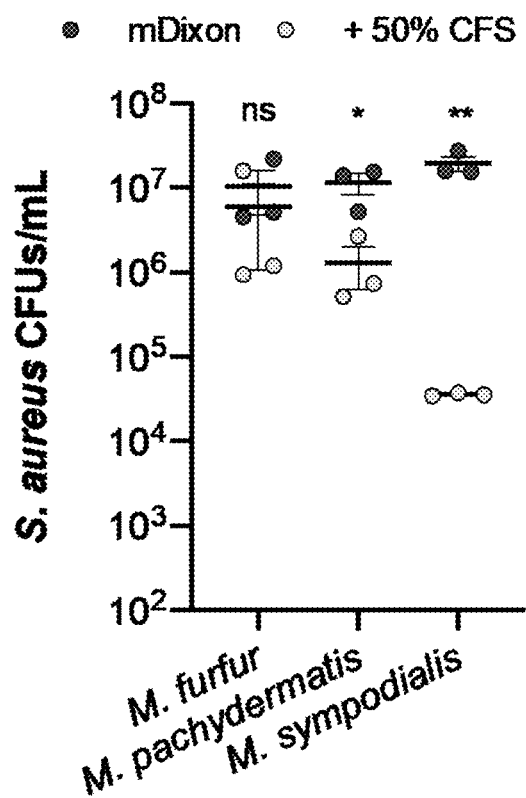
Figure 1C:
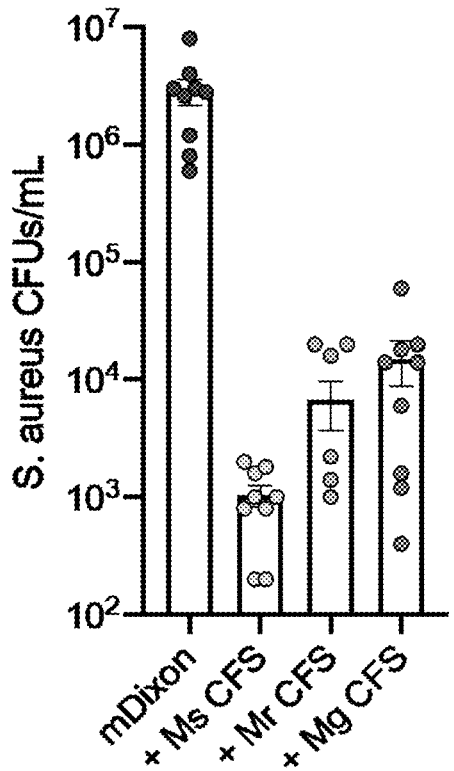

*Malassezia sympodialis* is the third most abundant species of *Malassezia* isolated from healthy human skin. In contrast,

*M. furfur* and *M. pachydermatis* are rarely isolated from healthy skin, and the latter is often found on canine skin. When tested for activity against the human bacterial pathogen *Staphylococcus aureus*, only the *M. sympodialis* isolate appeared to inhibit *S. aureus* growth. To assay this antagonism, the three yeast species were grown on agar plates for 72 hours until large colonies had formed. Adjacent to the yeast colonies, *S. aureus* was inoculated and incubated for 24 hours. While *S. aureus* was capable of growth adjacent-to, and in-contact-with, the *M. furfur* and *M. pachydermatis* colonies, it was unable to grow adjacent to *M. sympodialis* (FIG. 1A). To confirm that an exoproduct of *M. sympodialis* was toxic to *S. aureus*, the yeast strains were grown in liquid shaking cultures. Cell-free supernatants (CFS) collected from *M. sympodialis* cultures after 96 hours were toxic to *S. aureus* when mixed 1:1 with fresh media. Two hours of exposure to the CFS of *M. sympodialis* resulted in greater than 100-fold reduction in colony forming units (CFUs) per mL compared to a pH-matched media control (mDixon) (FIG. 1B). Similar results were observed with *M. restricta* and *M. globosa* (FIG. 1C). This is contrasted to *M. furfur* CFS which was non-toxic to *S. aureus* and *M. pachydermatis* CFS. which was only slightly toxic to *S. aureus* (FIG. 1B). These in vitro data suggest that *M. sympodialis* possess antimicrobial activity against *S. aureus*.

Figure 2A:
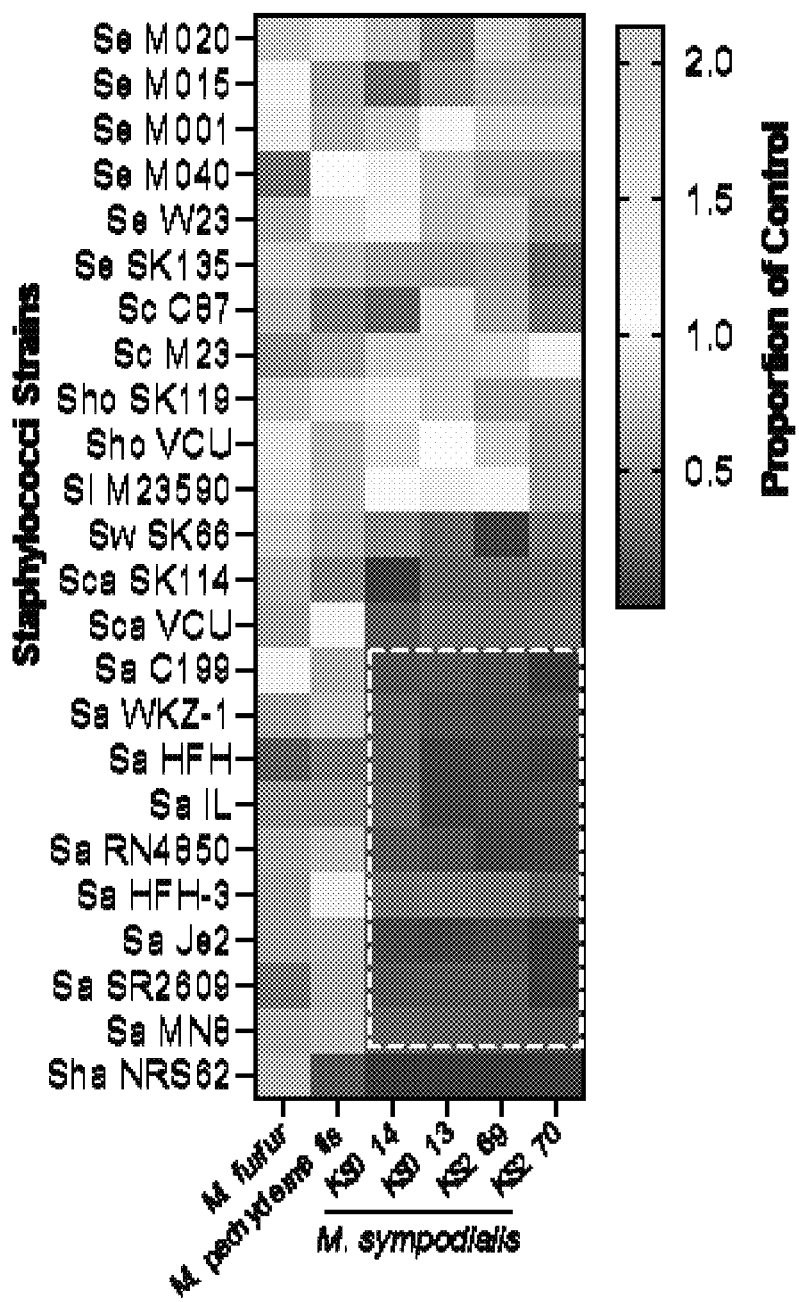
FIGS. 2A and 2B show antimicrobial activity of *M. sympodialis* targets particular staphylococci.

To determine if *S. aureus* sensitivity to *M. sympodialis* exoproducts is conserved across *S. aureus* strains, nine clinical strain of *S. aureus* were treated with 50% CFS from *M. furfur*, *M. pachydermatis*, or four strains of *M. sympodialis* (KS014, KS013, KS269, and KS270). All four strains of *M. sympodialis* produced exoproducts toxic to *S. aureus* strains, and all of the nine *S. aureus* strains were sensitive to treatment with the CFS from *M. sympodialis*. As observed above, CFS collected from *M. furfur* and *M. pachydermatis* were non-toxic or less toxic to *S. aureus* compared to those from *M. sympodialis* (FIG. 2A).

Figure 2B:
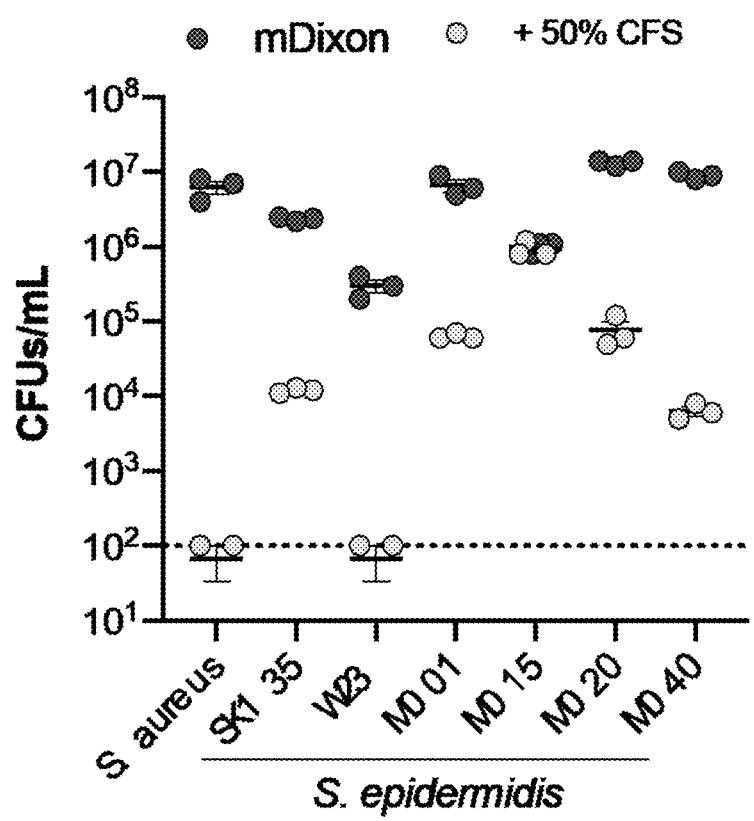

While *S. aureus* is considered a transient colonizer of healthy human skin, diverse coagulase-negative staphylococci are part of the normal skin flora and would likely share niches with skin resident *Malassezia* species like *M. sympodialis*. In accordance with this observation, many skin-resident commensal staphylococci are not sensitive to treatment with CFS from *M. sympodialis* (FIG. 2A). The most abundant staphylococci on healthy human skin is *S. epidermidis*. Interestingly, *S. epidermidis* sensitivity to CFS treatment from *M. sympodialis* was heterogenous; with some strains as sensitive as *S. aureus* (*S. epidermidis* W23) and some completely resistant (*S. epidermidis* M015) (FIG. 2B).

Example 3

Characterization of *M. sympodialis* Antimicrobial Effector

Figure 3A:
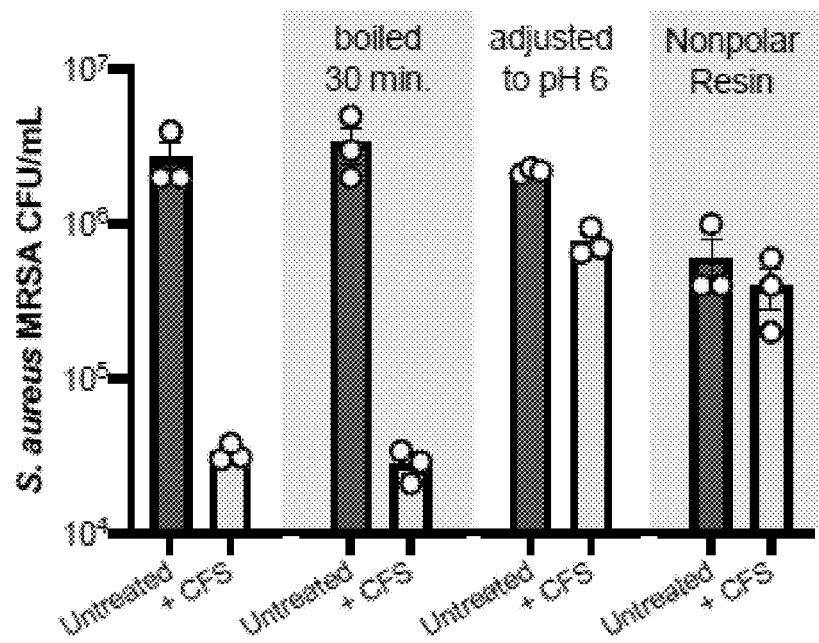
FIGS. 3A and 3B show characterization of antimicrobial activity produced by *M. sympodialis*.

To identify the toxic effector produced by *M. sympodialis*, the CFS, or mDixon media, was subjected to various treatments in an attempt to abolish toxicity. The toxic effector was found to be heat stable as the CFS retained toxicity after boiling for 30 minutes (FIG. 3A). This suggests that the toxic effector is non-proteinaceous. Additionally, the toxicity of the CFS was greatly reduced when the pH of the CFS was adjusted to pH 6 from pH 5.4-pH 5.6, suggesting that the effector could be ionic and that toxicity relies on ionization/deionization of the compound (FIG. 3A). Lastly, the compound can be removed from the CFS through treatment with a non-polar resin that binds organic compounds with molecular weight <2,000 (FIG. 3A). Furthermore, the compound can be eluted from the resin beads in greater than 75% methanol (data not shown). While the size of organic compounds known to bind this resin are small, the antimicrobial component of the CFS was retained above a 30 kDa molecular weight filter, suggesting that the compound aggregates in aqueous solutions (data not shown). Based on these data, the toxic effector appears to be a small, highly non-polar, non-proteinaceous organic compound.

Figure 3B:
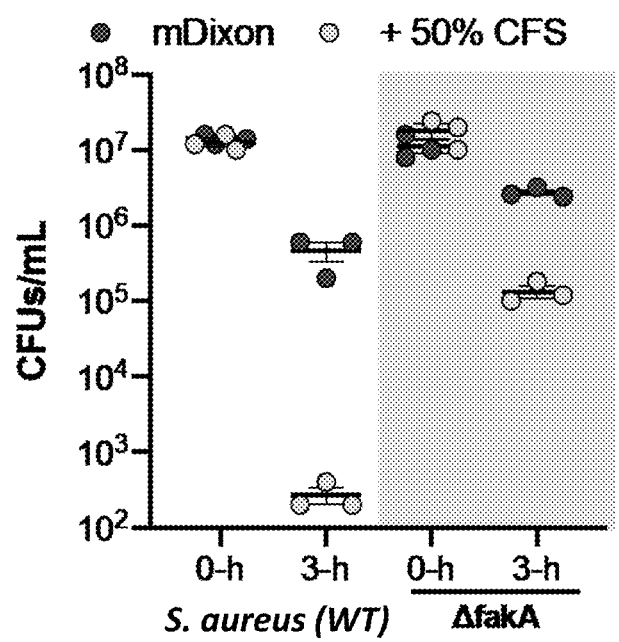

To determine the mechanism by which CFS from *M. sympodialis* kills *S. aureus*, CFUs from *S. aureus* were enumerated immediately after CFS exposure (t=0) and 3 hours after exposure. While there was no difference in CFU/mL between the CFS-exposed and control groups at 0 hours, there was a <10,000-fold reduction in *S. aureus* CFU/mL at 3 hours after CFS exposure compared to 0 hours (FIG. 3B). These data indicate that the CFS was bactericidal to *S. aureus*, meaning the bacteria are dying rather than simply not growing. Additionally, *S. aureus* did not grow during the 3 hour exposure to media that was pH-matched to the CFS (mDixon), and there was some toxicity to *S. aureus* when exposed to the media on its own, likely due to known small amounts of antimicrobial fatty acids that make up the media. Many antimicrobials that are bactericidal to non-growing bacteria target the cell membrane. Screening selected transposon insertion mutants from the Nebraska Transposon Mutant Library of *S. aureus* for genes involved in cell-membrane homeostasis for altered CFS sensitivity led to the observation that loss of function of the fatty acid kinase (fakA) resulted in reduced CFS sensitivity. A clean deletion of fakA in *S. aureus* (ΔfakA) confirmed that loss of the fatty acid kinase reduced CFS-sensitivity of *S. aureus* (FIG. 3B). Fatty acid kinase is required for incorporation of exogenous fatty acids into the cell membrane of *S. aureus*. This observation further supports the hypothesis that the bactericidal activity of the *M. sympodialis* CFS targets the cell membrane of *S. aureus*.

Example 4

Evolution of *S. aureus* Resistance to Antimicrobial Activity

Figure 4A:
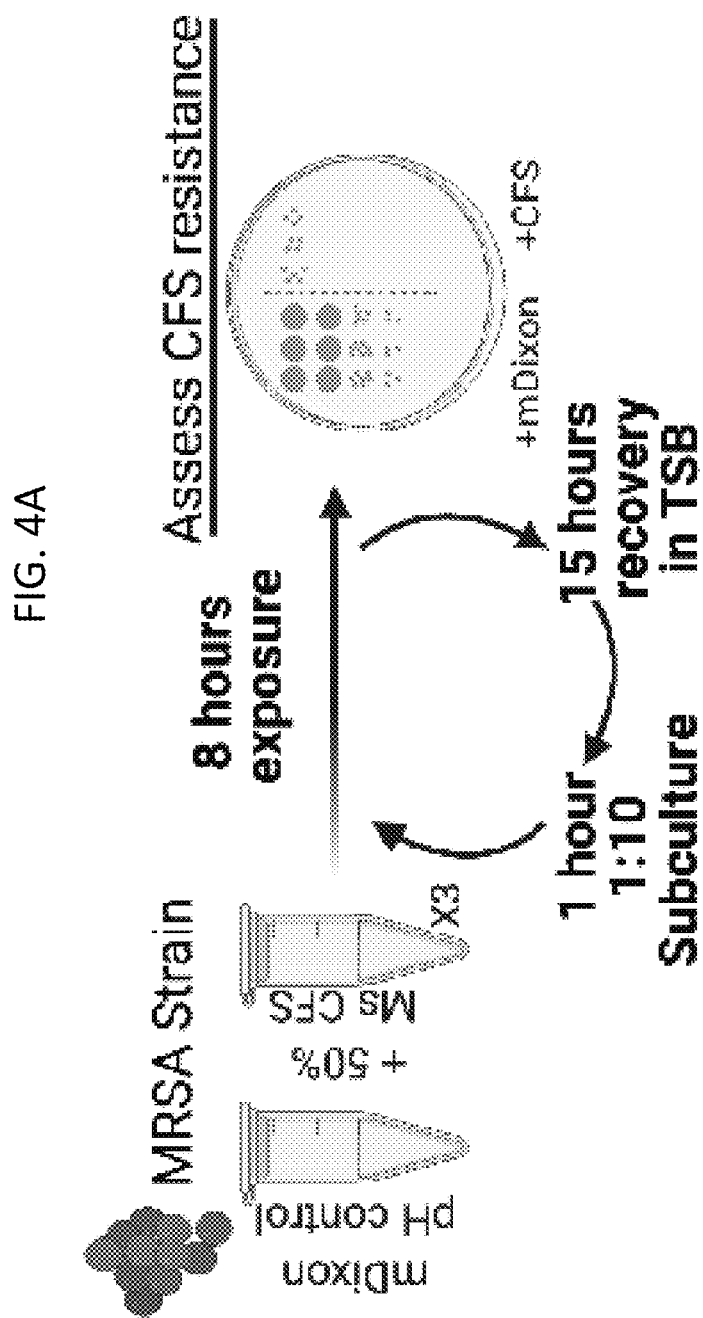
FIGS. 4A-4E show *S. aureus* adapts to serially exposure to CFS through mutation in the stringent response regulator Sa-Rel.
Figure 4B:
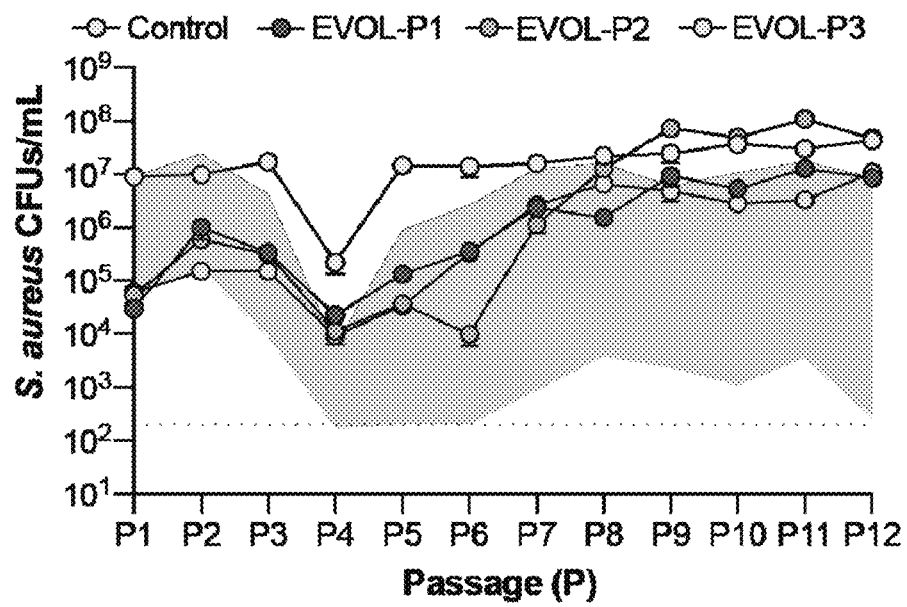

In order to determine how *S. aureus* may evolve resistance to the antimicrobial activity of *M. sympodialis*, a methicillin-resistant *S. aureus* strain was experimentally evolved through serially exposure to *M. sympodialis* CFS as depicted in FIG. 4A. After each exposure, or passage, in CFS or pH-matched media control, the CFUs were enumerated from a total of 12 passages. While the CFUs recovered from the control, pH-matched media, condition largely were unchanged throughout the 12 passages, the CFUs recovered from the CFS-treatment populations gradually increased (FIG. 4B). This observation suggests that resistance to *M. sympodialis* CFS can evolve rapidly in *S. aureus*.

Figure 4C:
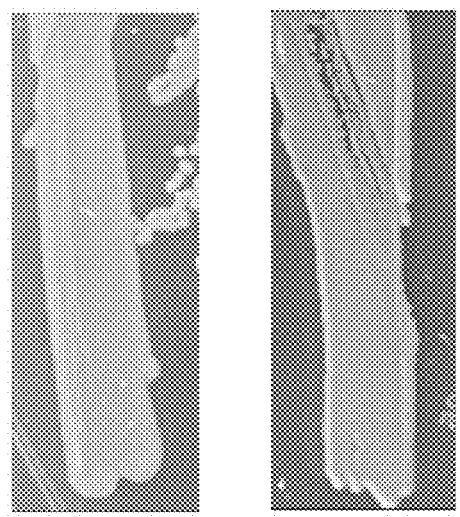
Figure 4D:
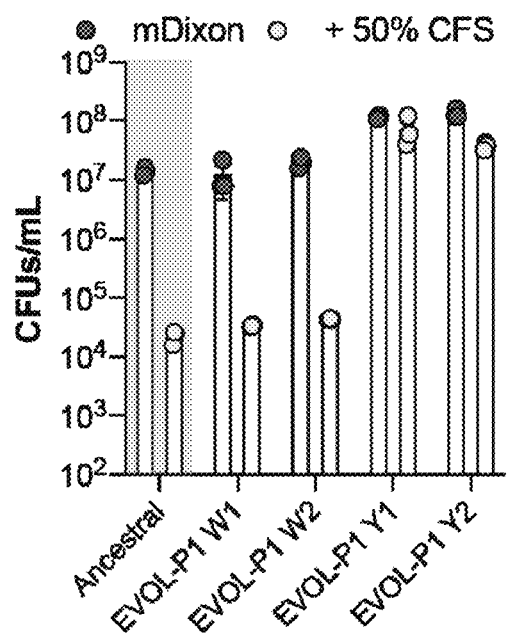

Within the passage 12 population of the EVOL-P1 replicate where *S. aureus* was exposed to *M. sympodialis* CFS, two distinct subpopulations were apparent: white, WT-like colonies and hyperpigmented yellow colonies (FIG. 4C). When individual clones from each of these subpopulations were selected and treated with *M. sympodialis* CFS, the white colonies were sensitive to the CFS treatment similar to the WT strain, while the yellow colonies were resistant to the CFS treatment (FIG. 4D). A similar hyperpigmented colony type was also isolated during an independent experiment where *S. aureus* was exposed to *M. sympodialis* yeast cells in a mixed biofilm. While the majority of *S. aureus* cells do not survive the co-culture, one replicate revealed surviving hyperpigmented cells similar to those identified through adaptation to the CFS (data not shown). This mixed-biofilm derived hyperpigmented isolate was also found to be resistant to treatment with *M. sympodialis* CFS (data not shown).

Figure 4E:
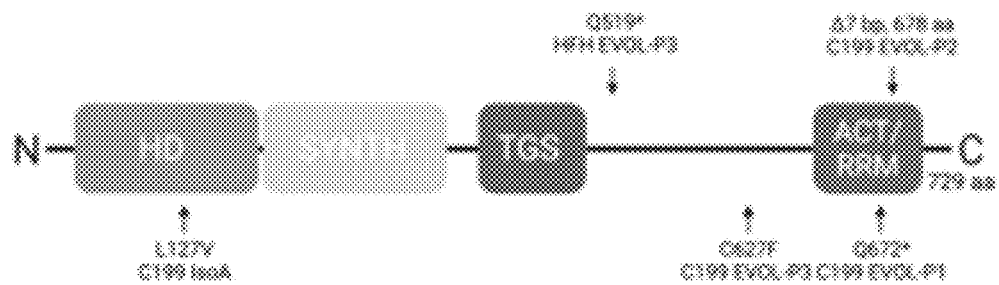

To determine the mutations underlying the CFS resistance of the hyperpigmented strains, both from the CFS-exposure experiment and the mixed-biofilm experiment, the genomes were sequenced and variant analysis performed. Within the EVOL-P1 replicate, the hyperpigmented isolates had mutations in the GTP pyrophosphokinase and master regulator of the stringent response Sa-rel (FIG. 4E). Sa-rel orchestrates the cellular response to nutrient limitation by altering numerous aspects of *S. aureus* physiology, including reduction in protein synthesis and amino acid metabolism. Interestingly, the two additional CFS-passaged populations contained hyperpigmented, CFS-resistant colonies with independent mutations in Sa-rel; as well as the isolate from the mixed-biofilm experiment (IsoA) (FIG. 4E). Lastly, when the experiment was performed with an independent strains of *S. aureus*, hyperpigmented CFS-resistant colonies were evolved that contained a mutation in Sa-rel. Together these data indicated that resistance to *M. sympodialis* CFS can evolve through mutations within the stringent response regulator Sa-rel.

Figure 5A:
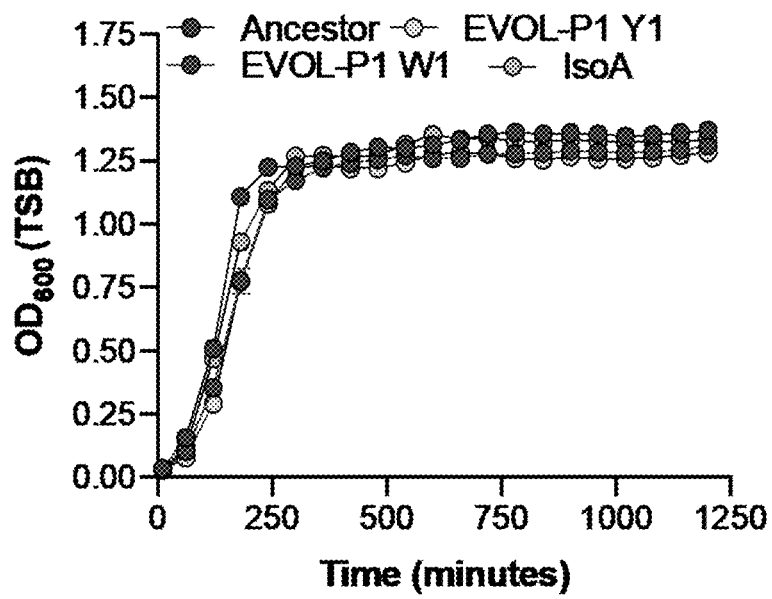
FIGS. 5A-5C show *S. aureus* growth in the presence of the β-lactam oxacillin. Growth in TSB with 0 μg/mL oxacillin (FIG. 5A), growth in TSB with 4 μg/mL oxacillin (FIG. 5B), and growth in TSB with 16 μg/mL oxacillin (FIG. 5C).
Figure 5B:
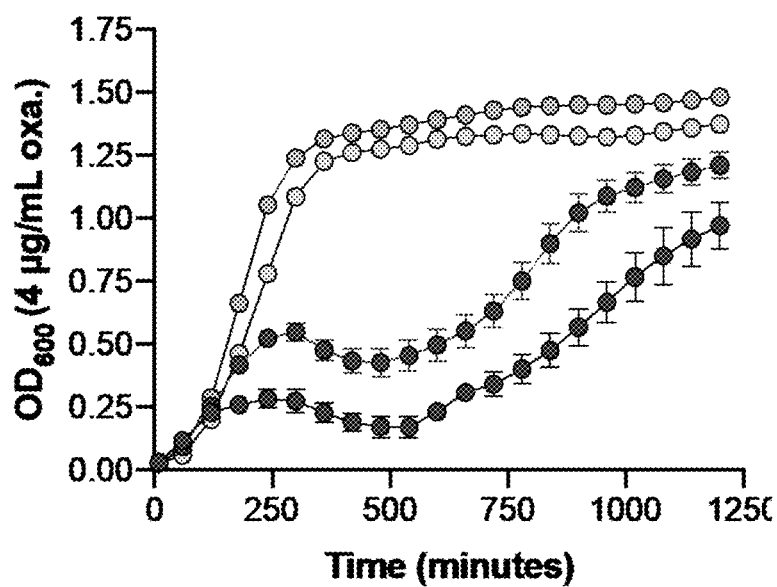
Figure 5C:
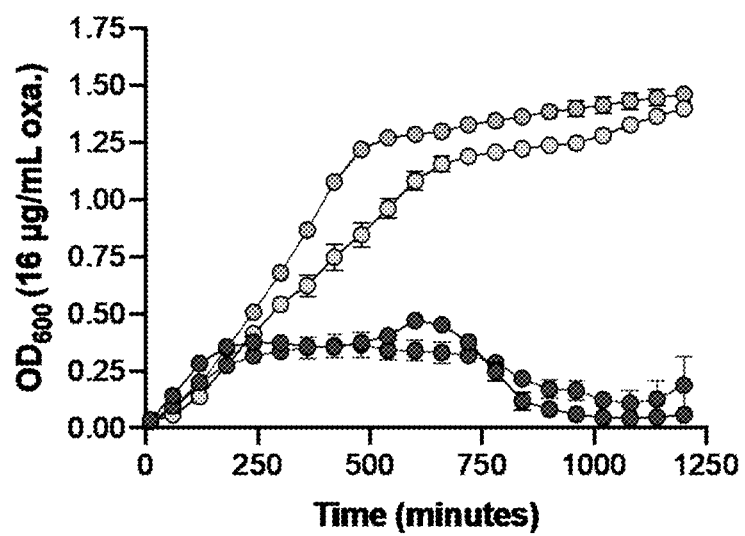

Low level activation of the stringent response is known to result in β-lactam homogenous resistance in strains of *S. aureus* that are already clinically considered to be resistant to β-lactam antibiotics. Homogenous resistance phenotypically resembles a 2-8 fold increase in minimum inhibitory concentration. To determine if the mutations in Sa-rel that confer CFS-resistance in *S. aureus* also confer homogenous, or hyper-resistance, to β-lactam antibiotics, the Ancestor and CFS-resistant strains were grown with super MIC concentrations of oxacillin. The oxacillin MIC for the ancestral strain was 4-8 µg/mL in rich media (tryptic soy broth, TSB). In TSB with 0 µg/ml oxacillin there was no difference in growth between the strains (FIG. 5A). However, at both 4 µg/mL (FIG. 5B) and 16 µg/mL (FIG. 5C) oxacillin, the CFS-resistant strains with Sa-rel mutations (EVOL-P1 Y1 and IsoA) were able to grow robustly while the WT, and WT-like strains (EVOL-P1 W1) were not. Interestingly, clinical isolates of *S. aureus* have been identified with similar Sa-rel mutations, low activation of the stringent response, and increased resistance to β-lactam antibiotics such as oxacillin. From these results, it is reasonable to hypothesize that the Sa-rel mutations that confer CFS-resistance in *S. aureus* also activate the stringent response and have additional consequences increased antibiotic resistance.

Example 5

Exoproducts from *M. sympodialis* Reduce *S. aureus* Skin Colonization

Figures 6A, 6B:
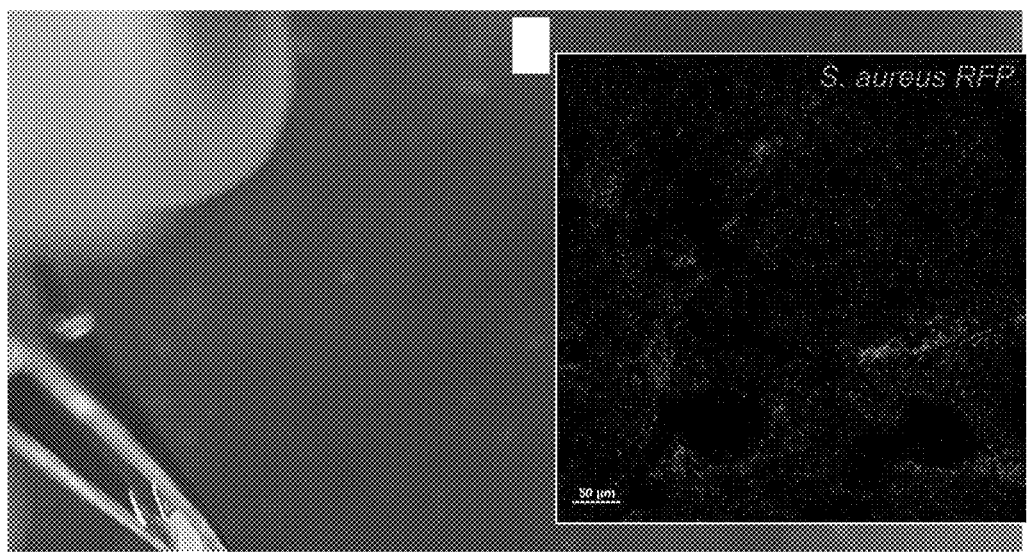
FIGS. 6A-6C show that *M. sympodialis* CFS reduces *S. aureus* survival on human skin explants.
Figure 6C:
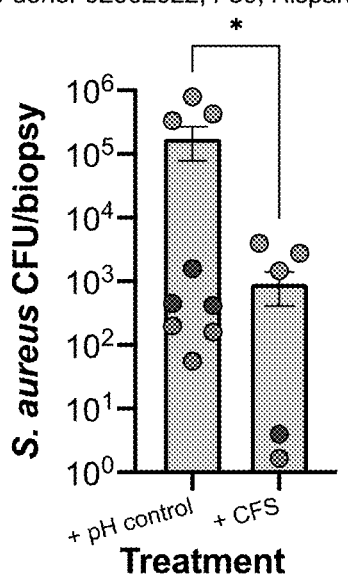

Three dimensional, living human skin biopsies provide the unique opportunity to study microbial interactions in the context of human skin (FIG. 6A). A strain of *S. aureus* expressing red fluorescent protein (RFP) is capable of colonizing the epidermal surface of such biopsies after 24 hours, as verified through fluorescent microscopy (FIG. 6B). Treatment of *S. aureus*-colonized biopsies with *M. sympodialis* CFS mixed 1:1 with PBS (+CFS) resulted in a significant reduction in recovered *S. aureus* CFUs compared to those treated with media (mDixon) mixed 1:1 with PBS (+pH control) across three independent skin donors (FIG. 6C). While there was inter-donor variability in the overall amount of recoverable CFUs from the '+pH control' condition, within each donor the treatment with *M. sympodialis* CFS reduced *S. aureus* CFUs by approximately 100-fold.

Example 6

In Vivo Testing of Inhibition of *S. aureus*

While this example describes methods utilizing *Malassezia* CFS, it is understood that the methods can also utilize *Malassezia* exoproducts and/or *Malassezia* cells.

In some examples, assessing the activity of *Malassezia* CFS in vivo utilizes a murine skin infection model in which the hair of mice is stripped with an adhesive (typically on the back). *S. aureus* from an overnight culture is then added to the skin surface. Over the course of several days an abscess is formed which can be measured to assess the severity of infection. *Malassezia* CFS is added directly to the skin surface both before *S. aureus* treatment or 1 day post infection in order to assess how the presence of *Malassezia* exoproducts impacts abscess growth. Control mice which are treated with *S. aureus* or *Malassezia* CFS alone are included as controls.

In addition to a skin infection model, a bacterial sepsis model may also be used in which mice are directly injected with live *S. aureus* retro-orbitally. Mice are treated with a formulation of *Malassezia* CFS via a tail vein injection during or after *S. aureus* infection. Survival of mice over the course of one week is monitored for both treatment mice and those treated with *S. aureus* or *Malassezia* CFS alone to determine protection from infection. Colony forming units of *S. aureus* is also measured from both whole blood and the spleen of sacrificed animals in order to measure *S. aureus* growth during infection.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of inhibiting bacterial growth, infection, and/or skin colonization in a subject, comprising administering to the subject a composition comprising:
   a *Malassezia* exoproduct, a *Malassezia* cell-free supernatant, or a *Malassezia* cell; and
   a pharmaceutically acceptable carrier.

2. The method of claim 1, wherein the bacteria is a *Staphylococcus* species.

3. The method of claim 2, wherein the *Staphylococcus* species is *S. aureus*, methicillin-resistant *S. aureus* (MRSA), vancomycin-resistant *S. aureus* (VRSA), *S. epidermidis*, *S. haemolyticus*, or *S. warneri*.

4. The method of claim 1, wherein the composition is administered orally or intravenously.

5. The method of claim 1, wherein the composition is administered topically.

6. The method of claim 1, further comprising administering to the subject an additional antibiotic therapy.

7. The method of claim 6, wherein the additional antibiotic therapy is administered to the subject prior to, concurrently with, or following treatment with the composition.

8. The method of claim 1, wherein the *Malassezia* is *Malassezia sympodialis*, *Malassezia restricta*, or *Malassezia globosa*.

9. The method of claim 2, wherein the method inhibits growth of the *Staphylococcus* by at least 10-fold compared to a control.

10. The method of claim 1, wherein the *Malassezia* exoproduct exhibits one or more of heat resistance, binding to non-polar molecules, and pH sensitivity.

11. The method of claim 10, wherein the pH sensitivity comprises antimicrobial activity at pH of about 6 or less.

12. The method of claim 1, wherein the composition comprises about 0.01%-10% w/w, 0.01-10% v/v, or 0.01-10% w/v of the *Malassezia* exoproduct, cell free supernatant, or cells.

13. The method of claim 1, wherein the composition further comprises an additional antibiotic compound.

14. The method of claim 5, wherein the composition is formulated as a solution, a gel, an ointment, a cream, or a suspension.

15. The method of claim 1, wherein the pharmaceutically acceptable carrier is a base comprising a plurality of inactive ingredients.

* * * * *